United States Patent [19]

Piotti

[11] Patent Number: 5,606,982
[45] Date of Patent: Mar. 4, 1997

[54] DEVICE FOR PUTTING ON CONDOMS AND THE COMPOSING SET WITH THE INCORPORATED CONDOM

[76] Inventor: Luis H. Piotti, San Martín 686-piso 7°of. 72, Buenos Aires, Argentina

[21] Appl. No.: 308,384

[22] Filed: Sep. 19, 1994

[30] Foreign Application Priority Data

Sep. 29, 1993 [AR] Argentina ................... 326169

[51] Int. Cl.⁶ ........................................ A61F 6/02
[52] U.S. Cl. .................. 128/842; 128/844; 128/918
[58] Field of Search ............................ 128/842, 844, 128/918; 604/330, 347–353

[56] References Cited

U.S. PATENT DOCUMENTS

| | | | |
|---|---|---|---|
| 3,282,414 | 11/1966 | Penksa | 128/844 |
| 4,856,534 | 8/1989 | Sorkin | 128/844 |
| 4,875,491 | 10/1989 | Parrone | 128/844 |
| 5,163,449 | 11/1992 | van der Valk | 128/844 |
| 5,318,551 | 6/1994 | Di Cristo | 128/844 |
| 5,327,911 | 7/1994 | Pien | 128/918 |

*Primary Examiner*—Michael A. Brown
*Attorney, Agent, or Firm*—J. Sanchelima

[57] ABSTRACT

There is provided a device for applying an elongated tubular condom to a male sex organ. The device has a body with lateral walls that define an annular inlet portion which forms an inlet mouth, an annular outlet portion which forms an outlet mouth, and a portion adjacent the annular outlet portion. The outlet and adjacent portions have respective diameters which permit the condom to be mounted on the body with a portion of the condom stretched over the outlet mouth and with a rolled portion of the condom in contact with the adjacent portion. The lateral walls of the body taper from the outlet portion to the adjacent portion so that, in use, the body can maintain the condom mounted thereon while permitting the rolled portion to unroll in contacting relation with the adjacent portion. The body has a cross section which is curvilinear. The device also has means to facilitate handling hereof.

11 Claims, 1 Drawing Sheet

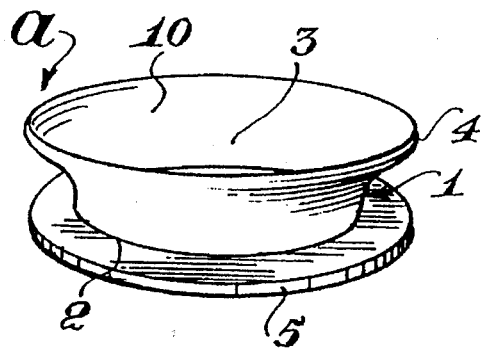
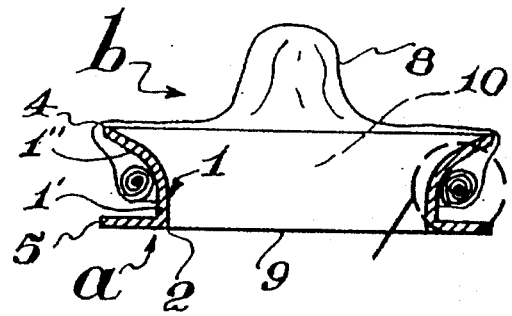
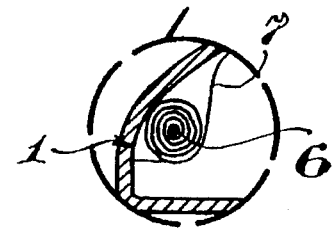
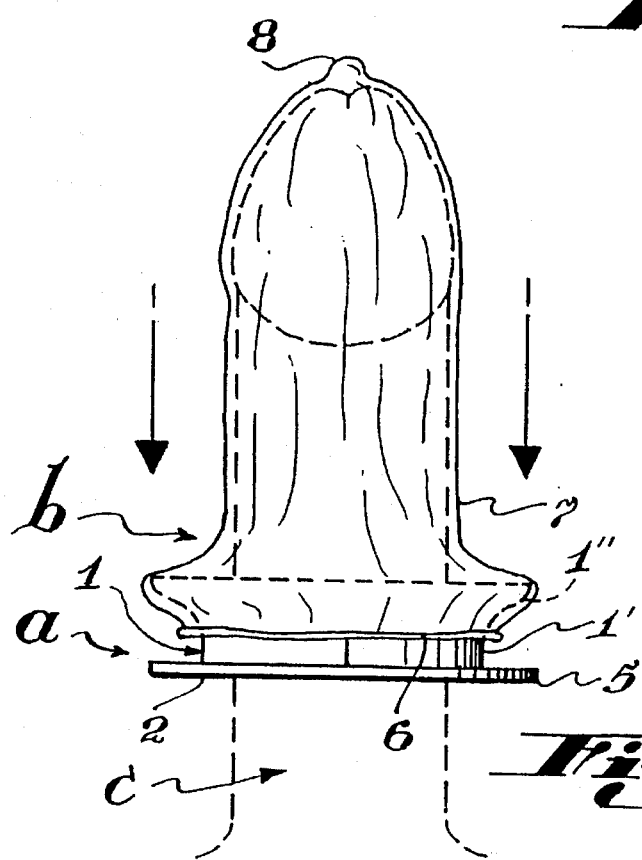

5,606,982

DEVICE FOR PUTTING ON CONDOMS AND THE COMPOSING SET WITH THE INCORPORATED CONDOM

FIELD OF INVENTION

The present invention refers to a device for putting on condoms and an apparatus incorporating a condom. The invention offers a practical and sure means for the employment of prophylactics.

BACKGROUND OF THE INVENTION

Condoms are known since long ago, which, through time have suffered diverse variations, have remained structured in the form of the penis, composed of an impermeable elastomer.

This condom, normally produced in latex, comprehends a tube that is shut at one end and prolongs itself with an appendix receptor of semen. In the opposite end, it comprises an annular cordon which forms an inlet mouth for a penis and constitutes the rolling nucleus of the packed condom.

It is widely known that the use of this type of protector involves a series of inconveniences, which results in reduced use of the condom.

Among the inconveniences is a fundamental fear of losing erection on the part of the man, due to the prolonged and complex procedure that putting on the condom entails. Putting on a condom interferes with the act, as it is not part of the act, but only preparation therefor.

On the other hand, aggressiveness in putting on a condom can involve stretching, pressures and handling of its own, such that aggressiveness can adversely impact the quality of the condom.

The invention referred to herein the description, brings about an ingenious and simple solution to the above problems, as it simplifies putting on the condom, and provides a practical, sure, docile and most of all, fast method.

SUMMARY OF THE INVENTION

The invention has as the main objects, a device for applying condoms and a condom placed in the applicator device ready for use.

To achieve the specified objects, a device for putting on condoms is provided to ease the application of each condom (b) unfolded all along the length of the penis (c). Each condom (b) is of the type that consists of a tubular, elongated and impermeable casing, which is made of an elastomer, and is closed at one end (10). The other end ends in an annular cordon (6) which constitutes the base of foldable laminar walls (7). The device is characterized by an annular body (a) having an external diameter larger than that of the condom (b) to be applied. The body has walls with even external faces and a delimiting border defined by an inlet mouth (9) to the internal part of the body or ring. The body progressively increases in diameter along its external face, until it ends in a border (4) delimiting an escape mouth (10) from a defined space.

BRIEF DESCRIPTION OF THE DRAWING

For better clarity and comprehension of the invention, reference is made to the drawing, in which the invention has been represented in some of the preferred embodiments, as follows:

FIG. 1 is a perspective view of the main body.

FIG. 2 is a cross section of the main body with the condom mounted thereon, showing a first cylindrical section perpendicular to the base of the walls near an inferior border.

FIG. 2a is a detail showing the rolled cordon of the condom, that remains disposed inside the condom, between the walls of the condom and the walls of the device.

FIG. 3 illustrates the way in which the condom is put on the penis, showing the position of the applicator device, and the direction in which the device is moved.

DETAILED DESCRIPTION

In the different figures, the same reference numbers indicate equivalent or corresponding parts, with various elements being marked with letters.

The reference characters identify the parts as follows:
(a)—main body (carrier of the condom)
(b)—condom
(c)—penis
(1)—lateral walls of the device (a)
(2)—delimiting border of the inlet mouth of the body (a)
(3)—space formed in the inside of the device (a), between its walls
(4)—delimiting border of the escape mouth of the body (a)
(5)—holding means
(6)—annular cordon formed by the folding of the walls of the condom
(7)—lateral walls of the condom
(8)—closed end of the condom
(9)—inlet mouth to the internal space (3) of the device (a)

In general terms, (a) is the main body of the device, which is designed to support and put on a conventional condom (b) along the length of a penis (c). Said conventional condom (b) is of the type that consists of a long and tubular impermeable casing (7) which is structured in an elastomer such as latex, and is closed at one end (8). The condom is provided with a hollow appendix as a spermatic receptor—while, at the opposite end, the laminar walls (7) end in an annular cordon (6) that constitutes the base of the laminar walls (7).

More particularly, and as can be seen in the drawing, the main annular body (a) is made of a material such as plastic or an appropriate, similar one, so as to reduce costs and make the unit disposable. It can also ease the displacement of the material of the condom on its surface.

This main body (a) of annular form has an external diameter much larger than the one of the condom (b) to be applied. The body has even lateral walls (1) originated in the delimiting border (2) of the inlet mouth (9) to the space (3) conformed between said walls (1) and ending in the border (4) delimiting the escape mouth (10) of said space (3). Lateral walls (1) include tapered section (1') and untapered section (1").

The body has a progressive enlargement of its external diameter that ends in the delimiting border (4) of the escape mouth (10).

Adjacent to the border (2), it has holding means (5) designed to facilitate the handling of the device.

These means can consist of an annular projection (5) that is found on the external walls, concentric with the delimiting border (2) of the inlet mouth.

For mounting of the condom (b) in the device (a), the cordon (6), formed by the folded condom, is stretched over the escape border (4), taking care that said cordon is disposed towards the inside of the condom, as shown in FIG. 2a, so that it remains between the latex of the condom and the lateral walls of the device.

Thus, mounting device (a), together with the condom (b) on the penis (c), involves introducing the device on the penis through the inlet mouth (9), lowering it down up to its base, as shown in FIG. 3, resulting in the condom (b) being completely displayed on the penis (c). Mounting can be interrupted, only if necessary, to release the cordon (6) of the condom from the escape border (4) of the device, so that the condom can be used during intercourse, with previous displacement of the applicator device.

In another embodiment, parts (a)–(b) may be provided preset between one another, thus providing the user with a condom already mounted on the applicator device.

In putting the present invention into practice, there is no doubt that modifications could be introduced respecting certain details concerning construction and shape without departing from the fundamental principles that are clearly recited in the following claims.

What is claimed is:

1. A device for applying an elongated tubular condom to a male sex organ, wherein the condom is formed of an impermeable, elastic material and has a closed end, an open end and a central sheath between the open and closed ends, said condom being extendible between a rolled position with at least a first portion of the central sheath rolled in a cordon at said open and an unrolled position with the cordon unrolled so that the at least one portion of the central sheath covers at least a part of the male sex organ, the device comprising: a) an annular body having a bore of sufficient size to permit the male sex organ to pass therethrough, said annular body having lateral walls comprising an annular inlet portion defining an inlet mouth, an annular outlet portion defining an outlet mouth and an adjacent portion between said inlet and outlet portions, said adjacent portion including a tapered section and an untapered section adjacent thereto, said outlet and adjacent portions having respective diameters sufficient to permit said condom to be mounted on said body in a mounted position with a portion of the central sheath stretched over the outlet mouth and with the rolled cordon contacting the adjacent portion, the body being configured with the tapered section tapering from said outlet portion to said untapered section such that, when the condom is in the mounted position and the closed end of the condom is extended in a direction away from the body, the body maintains the condom in the mounted position over said untapered portion while permitting the cordon to unroll and said tapered section preventing said cordon from separating; and b) means for facilitating handling of the device.

2. A device as claimed in claim 1 wherein said means for facilitating handling of the device, comprises an annular projection adjacent said annular inlet portion.

3. A device as claimed in claim 1 wherein said body is curvilinear in cross section with the outlet portion having a diameter greater than a diameter the inlet portion.

4. A device as claimed in claim 3 wherein said body is a single integral piece.

5. A device as claimed in claim 4 wherein said body inlet and outlet mouths are separated by a distance at least twice as great as a height of the rolled cordon.

6. An apparatus comprising: a) an elongated tubular condom for a male sex organ, said condom being formed of an impermeable, elastic material and having a closed end, an open end and a central sheath between the open and closed ends, said condom being extendible between a rolled position with at least a first portion of the central sheath rolled in a cordon at said open end and an unrolled position with the cordon unrolled so that the at least one portion of the central sheath covers at least a part of the male sex organ; and b) an applicator device comprising: i) and annular body having a bore of sufficient size to permit the male sex organ to pass therethrough, said annular body having lateral walls comprising an annular inlet portion defining an inlet mouth, an annular outlet portion defining an outlet mouth and an adjacent portion between said inlet and outlet portions, said adjacent portion including a tapered section and an untapered section adjacent thereto, said outlet and adjacent portions having respective diameters sufficient to permit said condom to be mounted on said body in a mounted position with a portion of the central sheath stretched over the outlet mouth and with the rolled cordon contacting the adjacent portion, said body being configured with the tapered section tapering from said outlet portion to said untapered section such that, when the condom is in the mounted position and the closed end of the condom is extended in a direction away from said body, said body maintains the condom in the mounted position over said untapered portion while permitting the cordon to unroll and said tapered section preventing said cordon from separating; and ii) means for facilitating handling of the device.

7. An apparatus as claimed in claim 6 wherein the open end of the condom is stretchable between a stretched and an unstretched position, and wherein the diameter of the outlet portion is such that the open end of the condom is stretched to the stretched position to mount said condom on the device in the mounted position.

8. An apparatus as claimed in claim 7 wherein the condom has an inner surface for contacting the male sex organ and an outer surface, said condom being mounted on said device such that, in the rolled position, the first portion of the central sheath is rolled in on the inner surface of the condom whereby only the outer surface of the condom contacts the adjacent portion of the device when the cordon unrolls.

9. An apparatus as claimed in claim 8 wherein the lateral walls of said body taper progressively from said annular outlet portion to said adjacent portion such that said body has a cross section that is curvilinear.

10. An apparatus as claimed in claim 9 wherein said body is a single integral piece.

11. An apparatus as claimed in claim 10 wherein the inlet and outlet mouths are separated by a distance at least twice as great as a height of the rolled cordon.

\* \* \* \* \*